US008345817B2

(12) United States Patent
Fuchs et al.

(10) Patent No.: US 8,345,817 B2
(45) Date of Patent: Jan. 1, 2013

(54) APPARATUS AND METHOD FOR NON-ROTATIONAL COMPUTER TOMOGRAPHY

(75) Inventors: Theobald Fuchs, Nuremberg (DE); Tobias Schoen, Nuremberg (DE); Randolf Hanke, Puschendorf (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 12/937,229

(22) PCT Filed: Apr. 9, 2009

(86) PCT No.: PCT/EP2009/002656
§ 371 (c)(1),
(2), (4) Date: Jan. 5, 2011

(87) PCT Pub. No.: WO2009/124774
PCT Pub. Date: Oct. 15, 2009

(65) Prior Publication Data
US 2011/0110487 A1 May 12, 2011

(30) Foreign Application Priority Data
Apr. 10, 2008 (DE) .......................... 10 2008 018 269

(51) Int. Cl.
*A61B 6/00* (2006.01)
(52) U.S. Cl. .................................. 378/10; 378/4; 378/57
(58) Field of Classification Search ................. 378/4, 10, 378/57
See application file for complete search history.

(56) References Cited

U.S. PATENT DOCUMENTS

| 5,095,501 | A | | 3/1992 | Kobayashi | |
| 5,475,726 | A | * | 12/1995 | Azevedo et al. | 378/4 |
| 5,872,828 | A | * | 2/1999 | Niklason et al. | 378/23 |
| 6,814,489 | B2 | | 11/2004 | Jensen et al. | |
| 2004/0247069 | A1 | * | 12/2004 | Arai et al. | 378/4 |
| 2008/0118024 | A1 | * | 5/2008 | Cho et al. | 378/13 |
| 2008/0285712 | A1 | * | 11/2008 | Kopans et al. | 378/26 |
| 2010/0278298 | A1 | * | 11/2010 | Hempel | 378/9 |

FOREIGN PATENT DOCUMENTS
EP 1627601 2/2006
WO WO2007/047114 4/2007

OTHER PUBLICATIONS

The English Translation of the International Preliminary Report on Patentability mailed Nov. 18, 2010 in parallel PCT application No. PCT/EP2009/002656, 5 pages.

* cited by examiner

*Primary Examiner* — Alexander H Taningco
(74) *Attorney, Agent, or Firm* — Michael A. Glenn; Glenn Patent Group

(57) ABSTRACT

A multi-dimensional representation of an object is obtained in that first and second pictures of the object illuminated using an X-ray source are created using a sensor that is located, in relation to the X-ray source, behind the object in a preferential direction defined by the relative positions of the object and of the sensor. A distance in the preferential direction between the X-ray source and the object is different in the first picture than in the second picture. The multi-dimensional representation of the object is obtained by combining the first and second pictures.

20 Claims, 6 Drawing Sheets

APPARATUS AND METHOD FOR NON-ROTATIONAL COMPUTER TOMOGRAPHY

CROSS-REFERENCE TO RELATED APPLICATION

This application is a U.S. National Phase entry of PCT/EP2009/002656 filed Apr. 9, 2009, and claims priority to German Patent Application No. 102008018269.9 filed Apr. 10, 2008, each of which is incorporated herein by references hereto.

BACKGROUND OF THE INVENTION

Embodiments of the present invention are concerned with an apparatus and/or a method for creating a multi-dimensional representation of an object, and, for example, they deal with how computer tomography image reconstruction methods may be employed without performing any rotational motions of the apparatus or of the object to be examined in small angular increments.

In computer tomography methods that are employed, for example, for diagnoses on human bodies or for testing materials in the industrial sector, an object to be examined is typically X-rayed by an X-ray source, wherein a sensor arranged opposite the X-ray source in relation to the object to be examined creates X-ray photographs of the object X-rayed. When employing an area sensor, the pictures thus created are two-dimensional, when employing a line sensor, they are one-dimensional. A multi-dimensional representation, i.e. for example a three-dimensional or a two-dimensional representation, is enabled in that the perspective from which the object is illuminated, or from which pictures of the object are taken, is changed. This involves taking pictures of the object from several perspectives. By changing the perspective, i.e. for example the angle from which the object to be examined is illuminated, information about an additional dimension, specifically depth information, i.e. positional information in a direction to the sensor surface, may be obtained from the projection pictures.

In diagnostic methods, it is customary to rotate the arrangement consisting of the X-ray source and the detector about a patient located at the center of the arrangement. In material testing methods, the object itself is often rotated, while the arrangement consisting of the sensor and the X-ray source remains stationary. To enable complete three-dimensional or multi-dimensional reconstruction of the object with the maximum spatial resolution available, tone may take pictures of projections of the object from a solid-angle range or from a plane-angle range of 180° in parallel-beam geometry. The angular increments of adjacent pictures also depend on the desired achievable spatial resolution, which is typically limited, in terms of hardware, by the resolution of the sensor used and by the precision of the mechanics.

In industrial material testing tasks, the objects to be examined are often so large that rotation of the detector arrangement about same or rotation of the object itself are out of the question for mechanical or cost reasons.

Even if rotation is possible, non-destructive testing of objects by means of the rotation-dependent computer tomography methods of 3D X-ray computer tomography, the achievable spatial resolution is frequently limited by mechanics. This results in a degradation of the spatial resolution, which may be several orders of magnitude higher than the actual achievable maximum spatial resolution, which is limited by the intrinsic sensor resolution of the sensor used. This results from the fact that for a full three-dimensional representation, tone may rotate the object or the apparatus relative to said object so as to measure projections from directions of at least 180°+plane angle. Particularly for large objects (e.g. freight containers or freight vehicles comprising containers), the mechanical rotational motion—even if it is possible, in principle—may be difficult, since large weights and/or large spatial dimensions may be moved with high precision and high repeating accuracy. This places extremely high demands on the adjustment and the precision of the axes used for mechanical movement.

Similar considerations apply to objects having unfavorable contours or envelopes that strongly deviate from the rotational symmetry (such as wings of airplanes or printed circuit boards, for example). With such flat, extensive objects, the distance between the focal spot of the X-ray source and the rotational axis cannot be selected to be arbitrarily small because said distance may be at least large enough so that the object, in its most unfavorable geometric extension, can be rotated or moved past the X-ray source. This results in a geometry-related limitation of the achievable resolution, it being possible for said resolution to be improved by optically magnifying the imaged elements of the object in that the source is brought close to the object to be examined, so that in accordance with the laws of ray optics, a magnified representation of the object is imaged on the sensor.

U.S. Pat. No. 6,814,489 B2 shows a rotational CT wherein the X-ray source and the sensor may be radially adjusted in relation to the object to be examined so as to set a magnification in the projection pictures produced by the apparatus.

The Japanese Publication "Study of New Linear Movement Tomography Using Magnification Ratio" describes a method wherein several X-ray photographs are taken of an object to be examined, while both the X-ray source and the X-ray sensitive sensor are moved relative to the object to be examined. Once the images have been corrected with regard to the different magnification ratios, the images thus obtained are added, said addition causing a blurring effect with regard to those picture elements that are not located within a plane in the object that is dependent on a displacement of the source and of the sensor. Thus, a two-dimensional picture is created by means of simple addition, wherein the contours of the objects in an advantageous plane are sharper than the contours of the objects in other image planes.

U.S. Pat. No. 5,095,501 proposes a CT method wherein use is made of two pairs of X-ray source and X-ray detector which are arranged at right angles to each other, so that the examination time for the patient may be halved.

European patent Application 1 627 601 A1 deals with a method of how stray artefacts caused by metallic implants within a patient's body may be suppressed by suitable image processing.

SUMMARY

There is a need for an apparatus and/or a method that enable examining objects and/or creating multi-dimensional representations of said objects without rotating the object in relation to the detector arrangement.

According to an embodiment, an apparatus for creating a multi-dimensional representation of an object may have: an X-ray source for illuminating the object; a sensor located, in relation to the X-ray source, behind the object in a preferential direction defined by the relative positions of the object and of the sensor, for creating a first picture and a second picture of the object; a mover for moving the source or the object so as to change a distance in the preferential direction between the X-ray source and the object between the first and second pictures; a combiner configured to determine, from the change in the distance between the first and second pictures, an angle of rotation which describes a rotation of the X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object.

According to another embodiment, a system for creating a multi-dimensional representation of an object may have: a first apparatus for creating a multi-dimensional representation of an object, which first apparatus may have: an X-ray source for illuminating the object; a sensor located, in relation to the X-ray source, behind the object in a preferential direction defined by the relative positions of the object and of the sensor, for creating a first picture and a second picture of the object; a mover for moving the source or the object so as to change a distance in the preferential direction between the X-ray source and the object between the first and second pictures; a combiner configured to determine, from the change in the distance between the first and second pictures, an angle of rotation which describes a rotation of the X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object; a second apparatus for creating a multi-dimensional representation of an object, which second apparatus may have: an X-ray source for illuminating the object; a sensor located, in relation to the X-ray source, behind the object in a preferential direction defined by the relative positions of the object and of the sensor, for creating a first picture and a second picture of the object; a mover for moving the source or the object so as to change a distance in the preferential direction between the X-ray source and the object between the first and second pictures; a combiner configured to determine, from the change in the distance between the first and second pictures, an angle of rotation which describes a rotation of the X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object; wherein the preferential direction of the first apparatus is perpendicular to the preferential direction of the second apparatus; and a common direction of motion so as to move the object in a direction of motion, which is perpendicular to the first and second preferential directions, in relation to the first and second apparatus.

According to another embodiment, a method of creating a multi-dimensional representation of an object may have the steps of: creating first and second pictures of the object illuminated using an X-ray source using a sensor that is located, in relation to the X-ray source, behind the object in a preferential direction defined by the relative positions of the object and of the sensor, a distance in the preferential direction between the X-ray source and the object being different in the first picture than in the second picture; and determining, from the change in the distance between the first and second pictures, an angle of rotation which describes a rotation of the X-ray source in relation to the object, which rotation corresponds to a change in the perspective from which the object is illuminated and imaged on the sensor; and combining the first and second pictures while using the angle of rotation and a computer tomography image processing algorithm in order to acquire the multi-dimensional representation of the object.

Another embodiment may have a computer program including a program code for performing the method of creating a multi-dimensional representation of an object, which method may have the steps of: creating first and second pictures of the object illuminated using an X-ray source using a sensor that is located, in relation to the X-ray source, behind the object in a preferential direction defined by the relative positions of the object and of the sensor, a distance in the preferential direction between the X-ray source and the object being different in the first picture than in the second picture; and determining, from the change in the distance between the first and second pictures, an angle of rotation which describes a rotation of the X-ray source in relation to the object, which rotation corresponds to a change in the perspective from which the object is illuminated and imaged on the sensor; and combining the first and second pictures while using the angle of rotation and a computer tomography image processing algorithm in order to acquire the multi-dimensional representation of the object, when the program runs on a computer.

Some embodiments of the invention enable obtaining a multi-dimensional representation of the object by imaging the stationary object by means of one or more translational motions of the X-ray source. The detector, or sensor, may be spatially arranged in various manners in relation to the X-ray source, or source. To enable imaging on the sensor, or the detector, said sensor or detector is located, within the optical path, behind the object to be examined. In some embodiments of the invention, the translational motions are effected in a direction perpendicular to the surface of the sensor or an apparatus used. In the event of a two-dimensional detector, this means in the direction of the surface normal, and in the event of a line detector, which is perpendicular to the line direction, this means in the direction of the surface normal of the pixels used in the line. In further embodiments, the motion is not performed exactly perpendicularly to the surface of the sensor, but a motion is performed in a preferential direction that is determined by a relative position of the object relative to the sensor. For example, the preferential direction may have an angle of, e.g., 22.5 or 45 degrees relative to the surface normal of the sensor elements.

In some embodiments of the invention, the apparatus for creating a multi-dimensional representation consists of an X-ray source used for illuminating the object, of a sensor for taking a projection picture of the object, and of a movement means that can move the object or the source so as to change a distance, in the preferential direction, between the X-ray source and the object, so that first and second pictures of the object may be taken at different distances. In relation to the X-ray source, the sensor is located behind the object in a preferential direction defined by the relative positions of the object and of the sensor. By changing the distance between the X-ray source and the object, the perspective from which the object is photographed is changed. This enables photographing various perspectives of the object without any rotation so as to obtain a three-dimensional representation of the object to be examined, for example when using a two-dimensional sensor, by combining the photographs.

In some embodiments of the invention, use is made of two X-ray sources that are movable independently of each other, that can be moved in the same preferential direction, but are arranged, in a direction perpendicular to the preferential direction (the movement direction of the X-ray sources), to be spatially separate from each other. By means of the arrangement, moving both X-ray sources in a step-wise manner may achieve that the object in its entirety or particularly interesting sub-areas of the object are photographed or imaged from perspectives spanning a range of angles of up to 180°.

In further alternative embodiments, this is enabled in that two detectors and two X-ray sources are used, said detectors and said X-ray sources being arranged such that they have preferential directions arranged at a right angle to each other. In this manner, imaging of the object from perspectives which comprise a range of angles of up to 180° may also be enabled.

In further embodiments of the invention, the preferential direction relative to the object to be examined may be changed in predefined or freely selectable angular increments, a plurality of X-ray photographs being taken, depending on the preferential direction, at different distances of the object from the X-ray source (distance in the preferential direction). To this end, for example, a movable axis or a movement means on which the X-ray source is arranged and on which the X-ray source may be moved in the direction of the object to be examined may be pivot-mounted. This additionally increases the spatial resolution in that the range of angles spanned is sub-divided into large angular increments, which are achieved by tilting the axis, and into small angular increments which are achieved by moving the X-ray source in the direction of the preferential direction. In this manner, it is possible to move the X-ray source close to, e.g., the surface of an extensive, non-uniformly shaped object so as to achieve high resolution while ensuring that the picture may be taken with a multitude of small angular increments, which is also useful for achieving high spatial resolution.

In further embodiments, the object to be examined may be guided past the apparatus—consisting of the sensor and the X-ray source—in a direction that is perpendicular to the advantageous direction, or parallel to the sensor surface, so as to enable, even with extremely extensive objects to be examined, to obtain a three-dimensional or multi-dimensional reconstruction of the entire volume of the object to be examined. In alternative embodiments, rather than moving the object past the detector or the apparatus, the stationary object is scanned with a mobile detector, so that, thus, the apparatus is moved while the object itself remains stationary.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
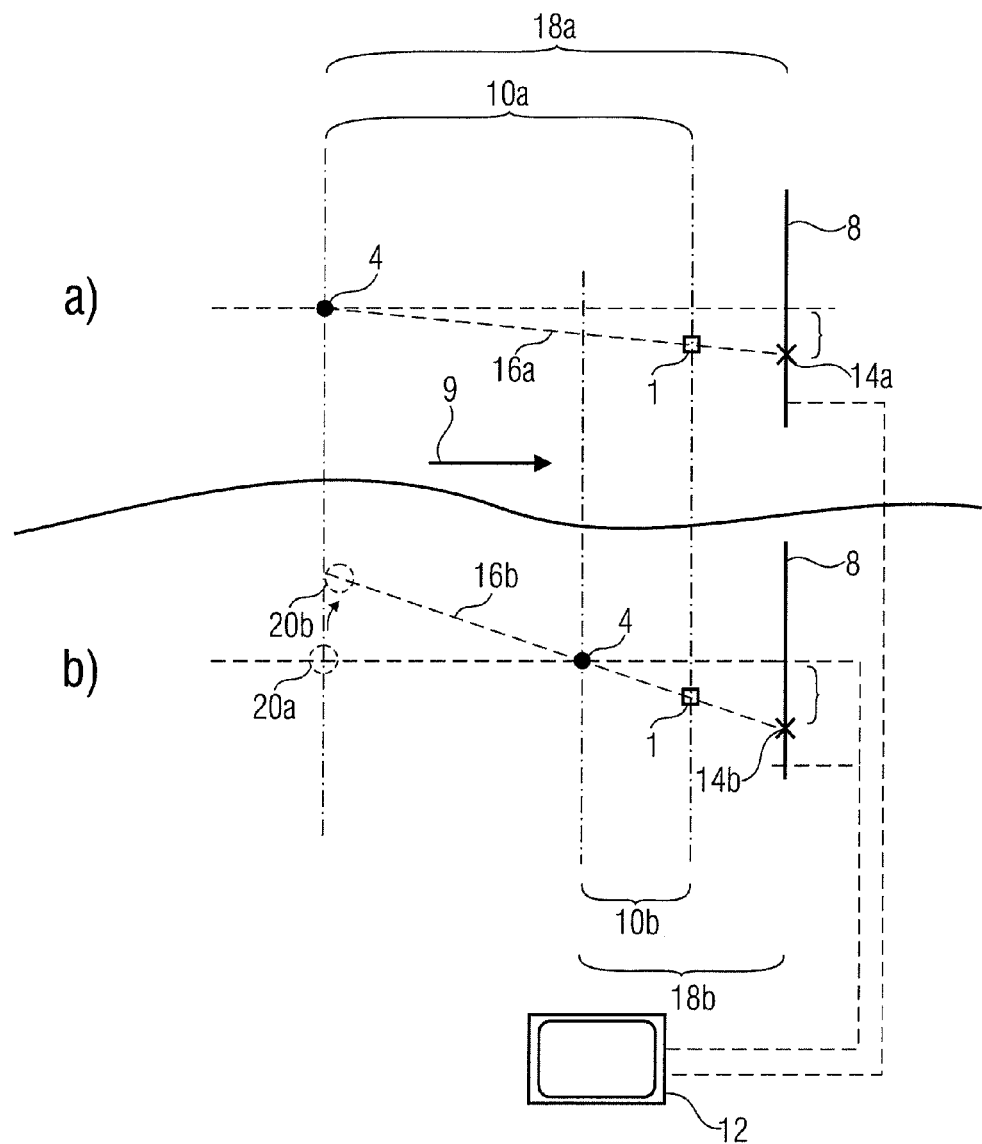
FIG. 1 shows an example of an apparatus for creating a multi-dimensional representation of an object.

FIG. 1 schematically shows an example of an apparatus for creating a multi-dimensional representation of an object 1. Said object 1, which may be located at any position within an observable measuring field 2, is illuminated by an X-ray source 4. A sensor 8 is located behind the object 1 with regard to a preferential direction 9, so that said sensor 8 may be used, when the object 1 is illuminated using the X-ray source 4, to take a two-dimensional or one-dimensional (when using a line sensor) picture, or to photograph a two-dimensional or one-dimensional (when using a line sensor) representation of the object.

The preferential direction is defined by the relative positions of the object 1 and of the sensor 8, and in the case shown in FIG. 1, it is perpendicular to the sensor surface of the sensor 8, i.e. parallel to the surface normal of the sensor elements of the sensor 8. The sensor 8 may be a matrix sensor or a line sensor, for example, which is sensitive to X-radiation, such as CCD elements coated with phosphorus, photo-multiplier arrays, or the like.

At the top (a), FIG. 1 shows a configuration wherein the X-ray source 4 is arranged at a first distance 10a from the object 1, whereas the second representation (b) shows a configuration wherein the X-ray source 4 is arranged at a second distance (10b) from the object 1.

FIGS. 1a and 1b show two configurations by means of which the two-dimensional position of the object 1 within the space may be determined when first and second pictures of the object are taken with the stationary sensor 8 being stationary. If both pictures are evaluated by means of a computer or a suitable combination means 12, the position of the object 1 within the space can be determined in the manner that will be briefly set forth below. To simplify the representation, it shall be assumed that the object 1 has a negligibly small spatial extension, so that the internal structures of the object 1 need not be resolved. Rather, full information about the object 1 will be obtained if its position in the preferential direction 9 and its position parallel to the sensor surface 8 are known. It shall be noted at this point that the considerations may be without restraint generalized to include an extensive three-dimensional or two-dimensional object when each volume or each spatially resolvable volume within the extensive object is equated with the object 1 discussed below.

The underlying concept, described by means of FIGS. 1a and 1b, of photographing two projections of an object 1 with different X-ray source positions resulting from translational motion may be transferred to standard computer tomography algorithms for image evaluation so as to thereby obtain spatially resolved two-dimensional or three-dimensional sectional pictures or representations of objects to be examined.

In the configuration represented in FIG. 1a, the X-ray source 4 creates a projection of the object 1 at the position 14a on the surface of the sensor 8. If the geometry of the arrangement is known, that is, the distance between the X-ray source 4 and the sensor 8, the "X-ray beam" 16a on which the object 1 may be located may be reconstructed by simple geometric considerations. However, because of the projection of the representation, one cannot see, if only one picture is taken, where the object 1 is located on the X-ray beam 16a.

The same applies when, with the configuration shown in FIG. 1b, a picture is taken that creates a projection of the object 1 at the position 14b on the surface of the sensor 8. In this case, too, reconstruction is possible only of an X-ray beam 16b which may have the object 1 located thereon.

However, if one knows the geometry of the apparatus, and, in particular, the distances 18a and 18b between the X-ray source and the X-ray sensor, or the positions 14a and 14b on the surface of the sensor 8, the information about the position at which, in the preferential direction 9, the object is located on the respective X-ray beams may be reconstructed. This reconstruction is also possible from a geometrical point of view if both X-ray beams are made to intersect.

At the intersection point, the object is located within the space. As has been said, this observation may also be generalized to include extensive objects that may be located in front of the sensor 8. In the event of a two-dimensional picture, three-dimensional reconstruction is also possible by obtaining the depth information from the two-dimensional projection in the above-described manner.

By combining the pictures with the different distances between the X-ray source 4 and the object 1, a multi-dimensional representation of the object 1 may thus be created.

For extensive objects, algorithms and/or image reconstruction methods known from computer tomography may be employed, in particular, since, as is outlined in FIG. 1b, the translation of the X-ray source 4 in order to change the distance 10a to the distance 10b is equivalent to rotating the X-ray source 4 of FIG. 1a about the new position of the X-ray source 4 in FIG. 1b.

In other words, a change in the perspective from which the object 2 is illuminated, said change being caused by a translation of the X-ray source as described in FIG. 1, may be equated with a rotation of the X-ray source 4 as is known from conventional CT methods.

What may be deduced from the translation of FIG. 1a to 1b is, in particular, the rotational motion, equivalent thereto, of the X-ray source 4 from the position 20a to the virtual position 20b.

If the rotational motion and/or the center of rotation are known, CT algorithms may thus be directly employed for calculating the three-dimensional or multi-dimensional representation of an object, it being possible to dispense with the necessity to rotate either the entire detector arrangement or the object. This has the advantages described above, in particular when examining large, extensive, heavy-weight objects wherein rotation is either not possible due to their geometric extensions, or wherein mechanical inaccuracy in controlling the angles of rotation, which is due to the mass of the objects, would result in a strong degradation of the resolutions of the CT pictures.

Looking at the schematic diagram shown in FIG. 1, it is self-evident that the reconstruction algorithms employed in the combination means need not necessarily comprise, as an intermediate step, conversion of the translational motion of the X-ray source 4 to the rotational motion outlined in FIG. 1b. Rather, it is also possible, of course, to rewrite the CT analysis algorithms so as to immediately extract or deduce, from the photographs taken of the sensor 8, the multi-dimensional representation when knowing the translational motion of the X-ray source.

It shall further be noted that it is not necessarily the X-ray source 4 that may be moved in order to achieve the change in perspective of the image, but that it is also possible, instead, to move the object 1 itself, in the preferential direction, away from or toward the X-ray source 4. Similarly to moving the X-ray source, as is outlined in FIG. 1, this also results in a change in perspective and thus enables extracting the depth information or the positional information in the direction of the preferential direction 9 from the pictures so as to thus achieve a multi-dimensional representation of the object.

In other words, FIG. 1 schematically illustrates the principle of reconstructing—in a three-dimensional and complete manner—the volume of an object 1 on the basis of one or more linear displacements or translational motions of the X-ray source 4 (or of the object 1) while dispensing with rotational motions of the object or of the apparatus as far as possible and while following conventional methods of computer tomography. As is depicted in FIG. 1, this is possible since in the event of a change in the perpendicular distance between the X-ray source and the object, while photographing several projections, the perspective will change, so that information about the internal structure of the object may be obtained, that is, in particular, depth information become accessible. This may also be referred to as translation CT, since the approach is equivalent to that of a CT, except that this examination dispenses with any rotational motions.

Figure 2:
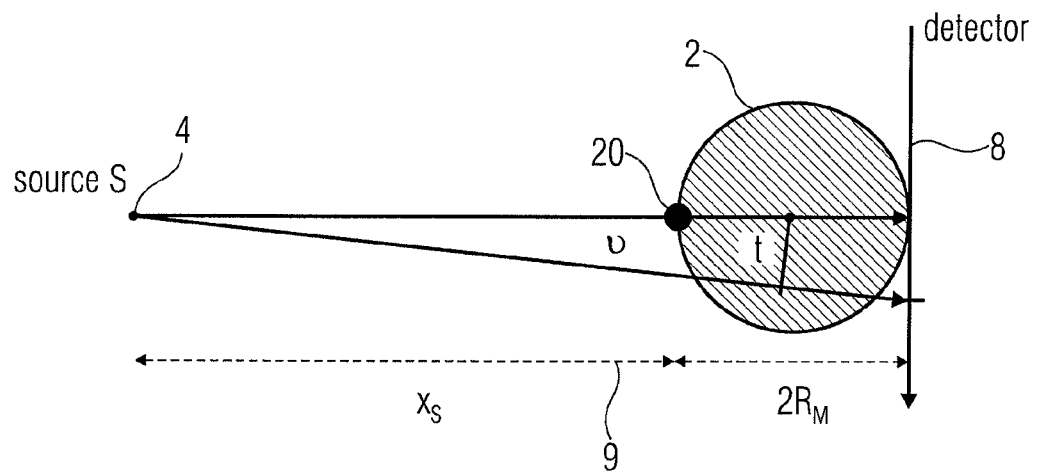
FIG. 2 shows a further example of an apparatus for creating a multi-dimensional representation.

FIG. 2 shows a further embodiment of an apparatus for creating a multi-dimensional representation of an object, wherein an object within a measuring field 2 is imaged by an X-ray source 4 to a detector 8, it being possible to move said X-ray source 4 in a direction perpendicular to the surface of the detector, or sensor, 8. In the case depicted in FIG. 2, an extensive measuring field 2 is contemplated to which the considerations described by means of FIG. 1 may also be applied, as was already described above.

The source 4 is moved toward or away from the sensor 8 (detector) in a preferential direction 9 so as to create a plurality of pictures that may be evaluated by means of a combination means, not shown here, or an evaluation computer so as to achieve the multi-dimensional representation of the measuring field 2.

FIG. 2 shows a possible arrangement that is symmetrical, i.e. wherein the central beam of an X-ray source 4, which, for the sake of simplicity, shall be assumed to be point-shaped, centrally impinges on the detector. That is, that beam that perpendicularly impinges on the detector surface will impinge on the center of same. A set of measurement data is obtained, for example, in that the projection image of the measuring field 2 on the sensor 8 is captured from a multitude of source positions (and, thus, perspectives) that differ by the distance $x_S$ from the measuring field 2. Of course, the measuring field 2 need not be spherically symmetrical or circular, as is depicted in FIG. 2. The measuring field 2 represented in FIG. 2 merely serves as a definition of that spatial region which is able to be processed at all using the arrangement of FIG. 2. Within this measuring field 2, any geometric arrangements or objects are feasible. Thus, the measuring field of FIG. 2 and the following figures depicted merely defines that area within which measurement may be performed in a useful manner with the apparatus contemplated in each case.

In other words, a two-dimensional measuring field is indicated in FIG. 2 as well as in the embodiments discussed in the following. However, the method and/or the apparatus discussed here may readily be supplemented in the direction perpendicular to the paper plane; data that may be used for three-dimensional reconstruction are recorded by a suitable line or flat-screen detector. If individual sensor lines are considered as being entirely independent of one another, the embodiments discussed here for the one-dimensional case may be directly applied to the two-dimensional sensor. In this analogous approach, the mutually independent lines provide data for corresponding layers through the object.

Of course, other volume CT methods may also be adapted to the principle of linear translational motion of the X-ray source or to the principle of changing the distance in order to detect an essential data domain for three-dimensional construction.

Two-dimensional reconstruction may evidently also be performed on the basis of a one-dimensional sensor.

On the basis of the pictures obtained at different distances between the object and the X-ray source in the preferential direction, filtering is performed by means of which multi-dimensional reconstruction of the object examined is effected. Said filtering is performed, e.g., by a combination means that applies a computer tomography image processing algorithm to the pictures thus created so as to obtain the multi-dimensional reconstruction. Said algorithm may comprise radon transformation, for example. In this context, in some embodiments of the invention, an angle of rotation is deduced from the translational motion in the preferential direction, which is caused by the movement means, said angle of rotation corresponding with the change in perspective that results from the translation with regard to the object imaged on the sensor. In accordance with some embodiments, the movement means is configured such that a predetermined fixed angular increment of the angle of rotation is generated by a single translational motion in each case. In other embodiments, the increments of the angles of rotation may be arbitrary, of course. That is, a series of a first picture, a second picture and several further pictures may be fabricated either with arbitrary angular increments and with equidistant angular increments so as to obtain therefrom a multi-dimensional reconstruction of the object by employing a computer tomography image processing algorithm.

In some embodiments of the invention, the apparatus for creating a multi-dimensional representation thus further comprises a sorting means which re-sorts the pictures taken of one series (at least of the first and second pictures) of pictures underlying a reconstruction such that they will be sorted by angular increments in a monotonously ascending or descending sequence, so as to make them available, thus processed, to a computer tomography image processing algorithm.

As was already mentioned above, the method and/or the apparatus for creating a multi-dimensional representation enable creating the representations with the maximally possible magnification (resolution), which is limited by the thickness of the object observed, by means of the translational motion of the X-ray source and/or by changing the distance between the X-ray source 4 and the object (or measuring field 2), even with extensive objects. This is so because it is possible to locally move the X-ray source close to the object to be examined, since the X-ray source may simply be moved away from the object again if a relatively thick part of the macroscopic object to be examined is to be examined. Due to the geometric magnification of the image on the sensor 8, a higher spatial resolution may thus be achieved for relatively thin objects. This is impossible for such objects when using methods or apparatus based on rotation, since in that case the distance of the X-ray source from the sensor is determined by the maximum geometric extension of the object to be examined.

In the case shown in FIG. 2 and also in the further embodiments described, the data is thus reconstructed by adapted algorithms of the filtered back projection and/or the algebraic methods corresponding therewith. Since by means of the principle proposed, the magnifications that may be achieved are of such large scale that it is no longer possible to image all of the regions of the measuring field 2 to be examined on the sensor (when the X-ray source 4 is located directly in front of the measuring field 2), methods of data supplementation or extrapolation and other reconstruction methods may be employed, for the highly magnified region (ROI=region of interest)—with regard to the data domain which in this case is incomplete—directly or possibly following adaptation to the geometric conditions (for example, on the basis of a wavelet or Hilbert transformation).

The available reconstruction methods may be subdivided initially into algebraic reconstruction methods and analytical reconstruction methods; for the analytical reconstruction methods, the geometrical boundary conditions, i.e. the distance of the X-ray source and the object from the sensor, for example, may be known. With a conventional type of reconstruction, a complete data set may be useful inasmuch as the object may be illuminated completely from a solid-angle range of 180° by means of parallel X-ray beams in order to enable complete image reconstruction from the pictures thus created. This is the case in particular since with this standard method, global operations acting on the entire object are used in each case for the data. By means of filtered back projection, the multi-dimensional picture of the object may be reconstructed if there is a complete set of data.

When the above-mentioned (projection) data is not fully available, or if part of this data is not useable, the data sets may be completed by extrapolation or interpolation so as to achieve a complete set of data which may be used as the basis for employing the standard reconstruction method.

Recent methods enable reconstructing, from incomplete data sets, sub-regions of the object to be examined by applying local operations. In this case, spatially local and frequency-local functions such as wavelets, for example, are used for analysis. Further methods that may operate on the basis of incomplete data sets use the differentials of the back projected data as well as a representation based on the Hilbert transformation of the image along specific X-ray lines in order to reconstruct the object within the ROI. All of these methods have in common that the geometric boundary conditions may be known, that is, it may be known how the X-ray beams of an (ideally) infinitesimal extension extend through the object. Such X-ray lines and/or beams are defined, for example, by the positions of the source and the read-out detector pixel.

A further class of reconstruction methods are algebraic methods, which achieve reconstruction by means of a numeric solution of a complex equation system by optimizing a model of the object examined. Said methods do not place any conditions upon the geometric boundary conditions, such as a range of angles to be covered or equidistant sampling of the projection images, but are highly computationally intensive, however, they are also applicable, in principle, within the context of the invention.

Figure 3:
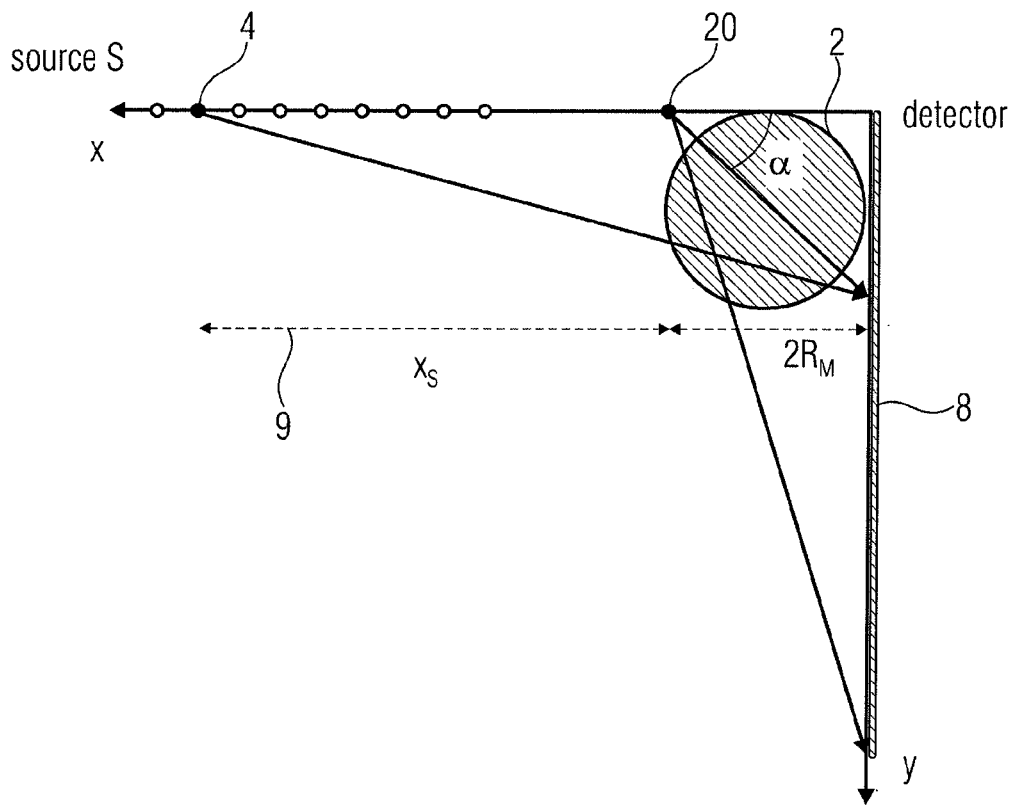
FIG. 3 shows a further embodiment of an apparatus for creating a multi-dimensional representation with an X-ray source at various positions.

FIG. 3 shows a further embodiment of an apparatus for creating a multi-dimensional representation of a measuring field 2, wherein the X-ray source may be moved to several positions schematically represented in FIG. 3. At each position, the measuring field 2 may be photographed from a different perspective, so that a multi-dimensional representation of a measuring field 2 may be created if the pictures taken from the different perspectives are combined.

In the embodiment shown in FIG. 3, all of the regions of the measuring field are photographed with different perspectives, except for the tangential central beam of the source. For mechanical reasons, there is a limit to magnification, said limit being defined by the minimum distance between the X-ray source 4 and the measuring field 2, said minimum distance being defined by point 20. For points and/or volumes within the measuring field 2 that are located on that side of the measuring field 2 that faces away from the X-ray source, changes in perspective of approximately 90° may be realized, since in the case of a remote source, the X-ray beam passing through said volumes impinges approximately perpendicularly to the surface of the detector, whereas, when the X-ray source is at the position 20, the same volumes are illuminated from a direction that is approximately parallel to the detector surface.

Since a resolution with which the depth information, i.e., the coordinate in the preferential direction 9, may be obtained depends on the range of angles under which the individual volumes of the measuring field 2 may be observed, the achievable spatial resolution or depth resolution differs in accordance with the observed partial volume of the measurement field 2. Since the variation in angles in the movement of the X-ray source increases as the distance from the axis on which the X-ray source is moved increases, the achievable depth resolution increases as the distance from the X-ray source increases. With the apparatus shown in FIG. 2, data within a range of angles that is approximately from 0° to 90° may consequently be measured by the translation of an individual X-ray source.

Figure 4:
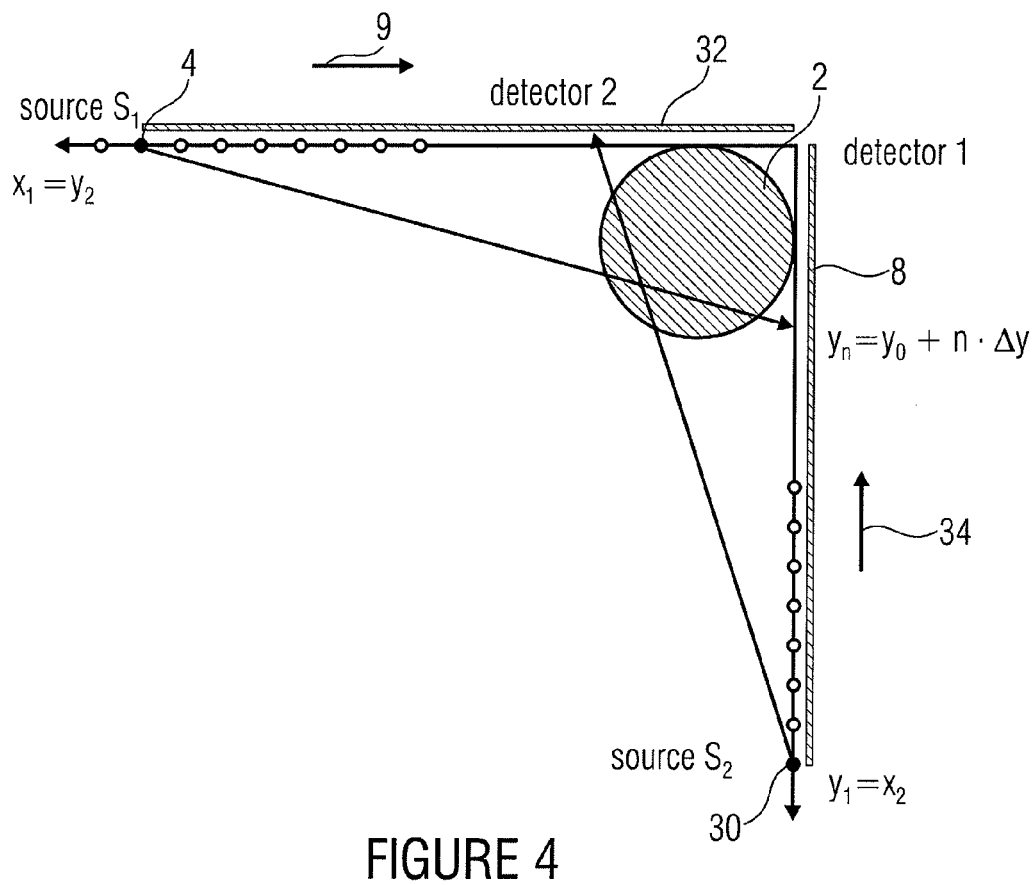
FIG. 4 shows a further embodiment of an apparatus for creating a multi-dimensional representation with two mutually orthogonal axes of possible X-ray source positions.

FIG. 4 shows a further embodiment of an apparatus for creating a multi-dimensional representation, wherein two mutually orthogonally aligned sources and sensors associated with them, respectively, may be moved independently of one another, so that by analogy with the above-described case, the range of perspectives from 0 to 90° may be doubled. Thus, pictures of the measuring field 2 may be taken from different perspectives that span an angle of approximately 180°. Displacement of both sources may be effected simultaneously or successively. When taking pictures simultaneously, one has to reckon with the fact that in the individual photographs, scattered radiation of those X-ray sources that are not associated with the corresponding sensors will occur, which on the whole may reduce contrast within the photograph.

In other words, the embodiment in FIG. 4 shows a second X-ray source 30 for illuminating the measuring field 2. The second X-ray source 30 may be moved with regard to a second preferential direction 34 perpendicular to the preferential direction 9 and defined by the relative positions of the object and/or the measuring field 2 and of a second sensor 32. By means of a second movement means, the second X-ray source 30 may be moved in the second preferential direction 34 so as to change a distance, in the second preferential direction, between the second X-ray source 30 and the measuring field 2. By analogy with the above-described method, a sequence of photographs of the measuring field 2 may be taken by means of the second X-ray source 30 and the second sensor 32 associated with it. During data evaluation by means of a combination means, the multi-dimensional representation is then obtained while using the photographs of the first sensor 8 and of the second sensor 32.

By using the two mutually orthogonally arranged sensors 8 and 32 with the X-ray sources 34 respectively associated with them, one may achieve, by varying the distances of the X-ray source from the measuring field 2 to be examined, that large volume fractions of the measuring field 2 to be examined may be observed approximately under a range of angles of 180°. This corresponds to the range of angles used for classical rotational CT, so that the corresponding image analysis algorithms and methods of CT rotational analysis may be used for evaluating or combining the photographs produced by means of the apparatus in FIG. 4.

Figure 5:
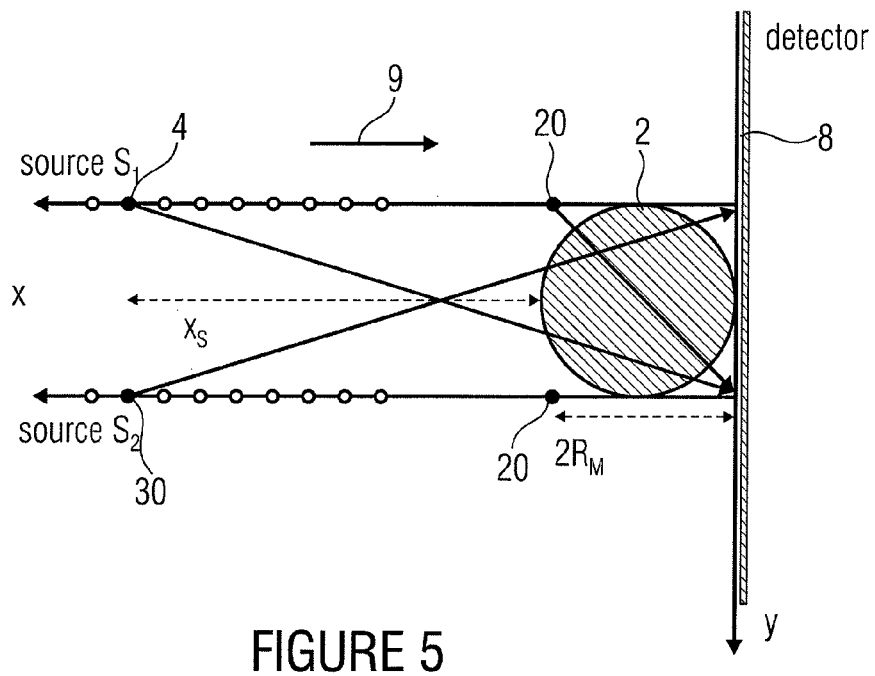
FIG. 5 shows a further embodiment of an apparatus for creating a multi-dimensional representation with two parallel axes of possible X-ray source positions.

FIG. 5 shows a further embodiment, wherein a first X-ray source 4 and a second X-ray source 30 are used, it being possible for the first and second X-ray sources to be moved in a preferential direction defined by the relative orientation of the measuring field 2 and of the sensor 8 so as to illuminate the measuring field 2 from different perspectives, so that perspectives from a range of angles of approximately 180° will be available when both X-ray sources 30 and 4 are moved from the points of the largest distance from the measuring field 2 to the points of the smallest distance 20. In other words, use is made of two X-ray sources 30 and 4, the travel paths of which are parallel on each side of the measuring field. The two data sets that are captured successively from the same distance of each source from the measuring field differ with regard to their beam angles and distances from the center of the measuring field in a mirror-symmetrical manner, so that data may result from a 180° range of angles.

Similarly to the embodiment discussed in FIG. 4, the embodiment depicted in FIG. 5 thus enables photographing a measuring field from highly different perspectives, it being possible for the measuring field of the embodiment shown in FIG. 5 to be highly extended, particularly in a direction parallel to the sensor 8, without impeding application of the inventive apparatus.

Figure 6:
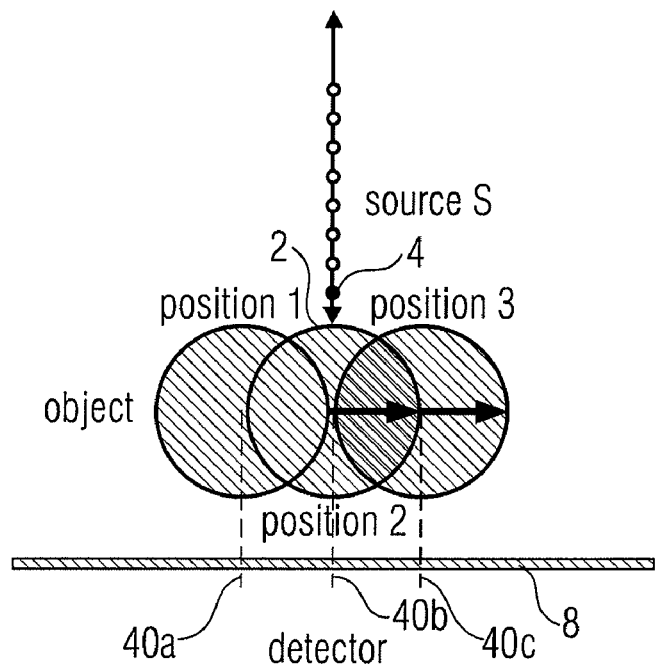
FIG. 6 shows a further embodiment of an apparatus for creating a multi-dimensional representation with object or source positions that differ in the lateral direction.

In particular, as is shown in FIG. 6, in case of an extensive measuring field, the measuring field may be moved past (in a lateral direction) the apparatus in relation to the sensor and to the X-ray source(s) 34 so as to measure the measuring field 2 from different perspectives. Thus, a multi-dimensional representation of the entire measuring field may be obtained, even if same cannot be fully captured within one measuring cycle.

By means of the example of using a single X-ray source, FIG. 6 shows the method and/or the apparatus which enable moving the measuring field 2 or the object past the measuring device in several iterations. Said moving past and/or said utilization of an additional translation means, which moves the object in a direction perpendicular to the preferential direction (in the lateral direction) so as to move it past, e.g., the sensor 8 and/or the X-ray source 4, is not limited to this embodiment. As is shown in FIG. 6 by way of example, the object or measuring field 2 may be guided past the X-ray source 4 and the detector 8 in several equidistant positions and/or steps 40*a*, 40*b* and 40*c*. Alternatively, it is also possible, of course, not to move the object in equidistant steps if deemed useful considering the geometric boundary conditions. Also, the lateral direction need not be perpendicular to the preferential direction in any of the embodiments. Said lateral direction may form any angle with the preferential direction, for example one or more angles between 20° and 70°.

In other words, a translation means as was described above may be employed with any of the remaining embodiments wherein one or more radiation sources are moved in relation to the object, with a stationary detector.

In addition, a translation means may be used for varying, in large angular increments, the perspective from which the object is photographed at the different positions of the translational motion, whereas small changes in perspective are effected by the movement of the X-ray source in the preferential direction. By combining large angular increments with small angular increments, the resolution may be improved even further.

Figure 7:
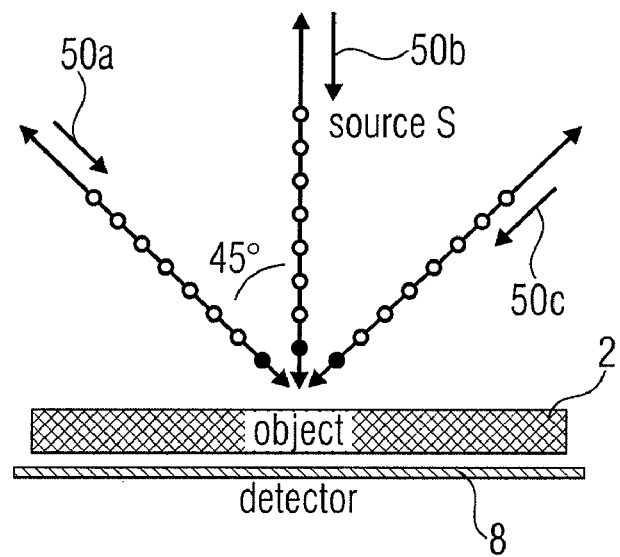
FIG. 7 shows an embodiment with a rotatably mounted X-ray source.

FIG. 7 shows a further embodiment by means of which the resolution may be improved further on the basis of this idea.

To this end, FIG. 7 schematically shows a rotation means by means of which the preferential direction in which the X-ray source is moved in relation to the object may be varied. When using such an apparatus or when applying a method corresponding to this apparatus, a measuring field 2 may be examined by means of a sensor 8 while using several preferential directions. FIG. 7 shows an example comprising three preferential directions 50a, 50b and 50c, which differ from one another by an angular increment of 45°, respectively. Major changes in perspective may thus be caused by tilting the preferential directions or the movement means guiding the source. The relatively small changes in perspective that are due to the movement of the X-ray source 4 of the preferential direction additionally provide the additional perspectives, in small angular increments, that may be useful for achieving high spatial resolution.

As an alternative to rotating or tilting the movement means, the measuring field 2 comprising the object itself may be tilted or rotated by the corresponding angular increments, which has the same effect. In other words, an embodiment schematically described by means of FIG. 7 may be used alternatively or additionally to the methods comprising several detector/source pairs, in which embodiment one or few rotational motions of the object or of the detector axis strongly improve the completeness of the data that may be useful for CT reconstruction, said rotation by the useful large angle (for example, the angle of 45° shown here) requiring a comparatively low level of precision. Alternatively, other angular increments, such as 22.5°, for example, may also be used, of course. Also in this case, alternatively, the object itself may be tilted once or several times by the corresponding angle in relation to the radiation source if the geometric boundary conditions allow for this.

Thus, complete reconstruction of an object to be examined within the measuring field may be achieved, using the inventive concept, by means of a rotation by few large angular increments. The number of projection directions, i.e. of rotations, is preferably smaller than 10, and in particularly advantageous embodiments smaller than 5. In advantageous embodiments, the angular increments of the rotation may be larger or smaller than 10°, i.e. considerably larger than in conventional rotation-based CT methods. The maximum range of angles under which the object is observed may be smaller than or equal to 90°, i.e. the maximum rotation may be smaller than 90°, it still being possible to achieve complete reconstruction within the ROI.

Figure 8:
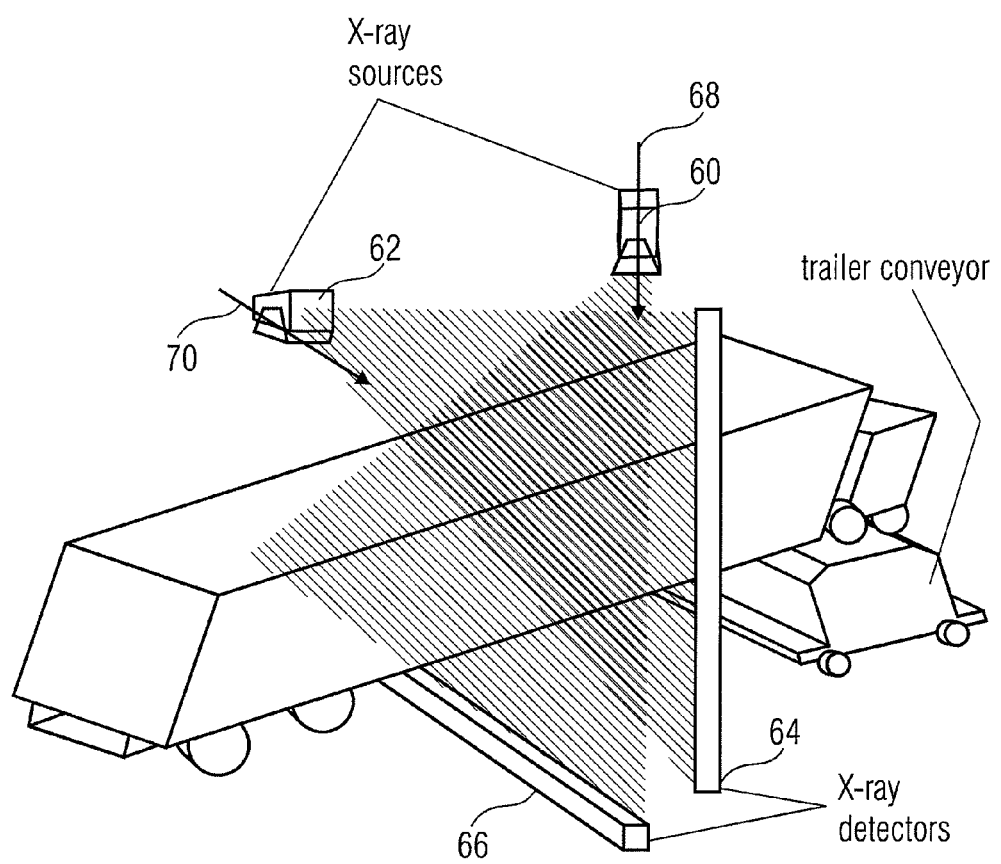
FIG. 8 shows an example of a system for creating a three-dimensional representation of an extensive object.

FIG. 8 schematically shows a possible application of the method and/or of inventive apparatus for examining freight containers and/or creating three-dimensional sectional images and/or representations of freight containers for mobile or stationary inspection. In this context, a system that may possibly already exist and consist of a first X-ray source 60 and a second X-ray source 62 and of X-ray detectors 64 and 66 that are associated with them on opposite sides of the object to be examined, respectively, may be expanded by implementing a movement device which enables moving the X-ray source 60 in the first preferential direction 68 and moving the second X-ray source 62 in the second preferential direction 70 relative to the container. When applying the above-described concept, three-dimensional representation of the contents of the container may be created.

Thus, for example, a system may be expanded wherein an object is already scanned, in layers, by means of two orthogonal sources (for example, two LINACS arranged at an angle of 90° relative to each other) and associated line and/or area detectors in that the regions to be examined are moved past the detectors. Alternatively, it is also possible to move the detector system past the regions to be examined. In the application scenario described by means of FIG. 8, one particularly striking advantage is that rotation of the detector components or of the object can be avoided, which for the containers described could be realized only at a very high expenditure, which may be dispensed with when employing the above-described concept.

Figure 9:
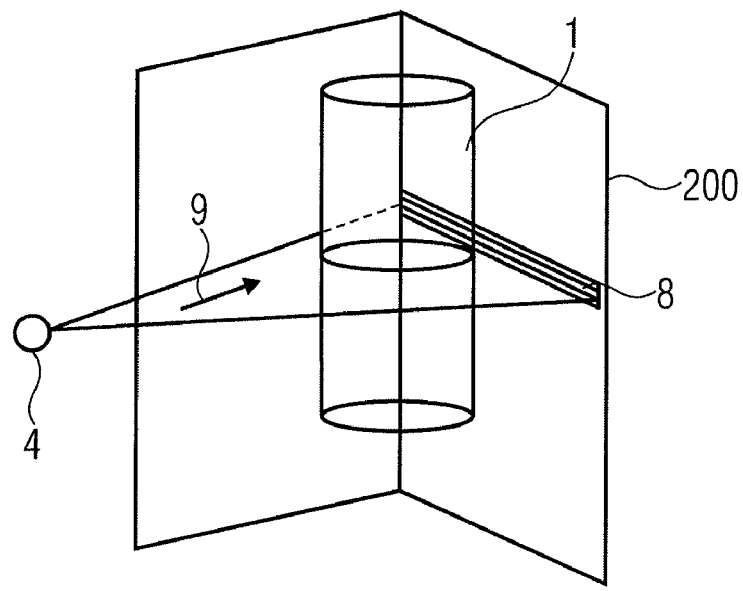
FIG. 9 shows an example of measuring a stationary tube.
Figure 10:
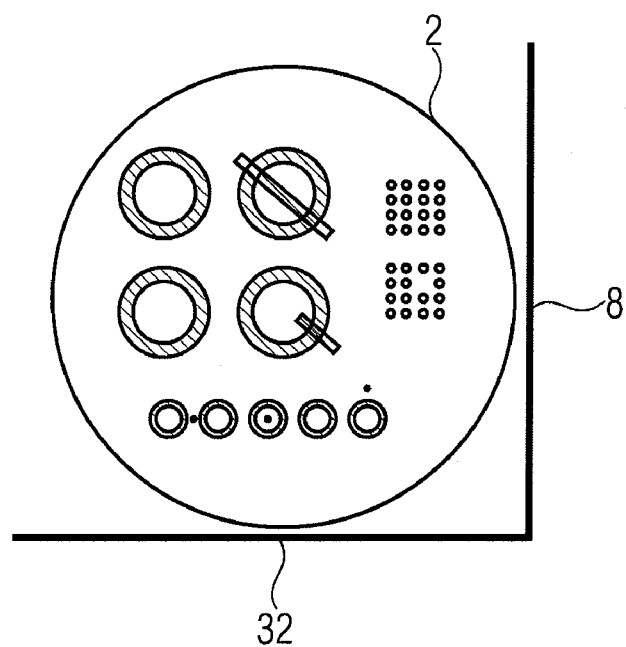
FIG. 10 shows a further example of measuring stationary objects.

FIGS. 9 and 10 show examples of applying the inventive concept for measuring stationary objects that cannot be rotated or moved due to their installation situation. The embodiments shown in FIGS. 9 and 10 are based on a spatial arrangement of X-ray sources and detectors as was already schematically depicted by means of FIG. 4, for example. Regarding the details of the evaluation, reference shall therefore be made at this point to the statements made above regarding FIGS. 3 and 4.

As an object 1 to be measured, FIG. 9 shows a tube installed in the corner of a wall 200—an installation position unfavorable to standard X-ray examination. As may be seen from the figure, the wall 200 prevents a rotational motion of the X-ray source 4 and of the detector 8 about the tube. However, when applying the inventive concept, the tube may nevertheless be multi-dimensionally measured in that the X-ray source 4 is moved in the preferential direction 9, as was already explained in detail by means of the schematic diagrams in FIGS. 4 and 5.

FIG. 10 shows a further possibility of industrial application, for example within a refining plant, where a multitude of tubes or cables that are located within the measuring field 2 and have different cross sections can be inspected simultaneously, for example when the arrangement outlined schematically is used which comprises two sensors 8 and 32 that are arranged at right angles to each other, as was also discussed, inter alia, by means of FIG. 4.

In summary, a method of creating a multi-dimensional representation of an object which implements the concept described in the present application may be described as follows.

Initially, first and second pictures of the object illuminated using an X-ray source are created using a sensor that is located, in relation to the X-ray source, behind the object in preferential direction defined by the relative positions of the object and of the sensor, a distance in the preferential direction between the X-ray source and the object being different in the first picture than in the second picture. In other words, said distance is changed between the first and second pictures. Consequently, a first picture will be taken with a first distance between the X-ray source and the object, whereupon a second picture is taken with a second distance between the X-ray source and the object.

To obtain the multi-dimensional representation of the object, the first and second photographs are then combined, it being possible to use, for X-ray tomography, image reconstruction algorithms that are adapted to the geometric conditions.

Even though in the above-described embodiments, a maximum of two different X-ray sources was used in each case, the concept described is also applicable to a larger number of X-ray sources, of course, e.g. the necessity of rotating the object or the axes of the preferential direction being dispensed with, in particular, when several sources are used.

As was already mentioned, it is also possible, as an alternative to changing the position of the X-ray source, to change the position of the object itself in the direction of the X-ray source so as to obtain the useful different perspectives of the image. In addition, it is possible to displace the detector if the object is stationary, so as to gradually change the magnification of the image and, thus, to possibly image individual regions of the object to be examined at a higher resolution.

This possibility may evidently also be combined, as an additional property, with any of the previously discussed embodiments.

In the above-described embodiments, a step size that is constant in each case was shown for moving the X-ray source or the object, for the sake of the simplicity of the representation. However, this results in a different change in the angle and, thus, in the perspective, respectively. In order to obtain, similarly to standard CT algorithms, an equidistant angular change per photograph, it is also possible to perform the translational motion of the source such that an equidistant angular change, i.e., a respectively constant change in perspective, results from this.

In some further embodiments, the translational motions may also be performed using robot arms, for example, which results in increased flexibility of the method in that the sources may also be employed with objects to be examined that are of extremely irregular shapes, in that motions of the X-ray source may be performed in any spatial degrees of freedom.

In summary, employment of the above-described apparatus and/or methods yields numerous advantageous. For example, an apparatus for performing highly precise rotational motions that is difficult to realize mechanically can be avoided. As a result, losses of resolution due to staggering of axes or misalignment of such complex mechanical apparatus may also be avoided, inter alia.

Also, objects having unfavorable geometries (for example, wings of planes or printed circuit boards) may now be subject to complete three-dimensional computer tomography while almost fully dispensing with moving said objects.

Depending on the conditions, the method of creating a multi-dimensional representation of an object may be implemented in hardware or in software. Implementation may be effected on a digital storage medium, in particular a disk or CD with electronically readable control signals which may cooperate with a programmable computer system such that the method of creating a multi-dimensional representation of an object is performed. Generally, the invention thus also consists in a computer program product having a program code, stored on a machine-readable carrier, for performing the inventive method, when the computer program product runs on a computer. In other words, the invention may thus be realized as a computer program having a program code for performing the method, when the computer program runs on a computer.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for creating a multi-dimensional representation of an object, comprising:
    a first X-ray source for illuminating the object,
    a second X-ray source for illuminating the object;
    a sensor located, in relation to the first X-ray source, behind the object in a preferential direction defined by the relative positions of the object and of the sensor, for creating a first picture and a second picture of the object;
    a mover for moving the source or the object so as to change a distance in the preferential direction between the first X-ray source and the object between the first and second pictures;
    a combiner configured to determine, from the change in the distance between the first and second pictures, an angle of rotation which describes a rotation of the first X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object;
    wherein the second X-ray source is located in the preferential direction in front of the object, wherein the mover is additionally configured to move the second X-ray source in the preferential direction so as to change a second distance in the preferential direction between the second X-ray source and the object; and
    wherein the sensor is additionally configured to create a third picture, wherein the object is illuminated by the second X-ray source, the combiner being configured to combine the first, second and third pictures so as to acquire the multi-dimensional representation of the object.

2. The apparatus as claimed in claim 1, wherein the preferential direction is perpendicular to a sensitive surface of the sensor.

3. The apparatus as claimed in claim 1, wherein a multi-dimensional representation is created which comprises information about an additional spatial dimension comprised neither by the first nor by the second pictures, so that at least one more spatial dimension may be imaged in the multi-dimensional representation than in the first and second pictures.

4. The apparatus as claimed in claim 1, wherein the combiner is configured to compensate for a change in the scale within the first or second picture which is due to the change in the distance in the preferential direction between the pictures.

5. The apparatus as claimed in claim 4, wherein the combiner is configured to compensate for a change in scale by a scaling factor dependent on the distance in the preferential direction.

6. The apparatus as claimed in claim 1, wherein the second X-ray source is arranged in front of the object with regard to a second preferential direction perpendicular to the preferential direction, said second preferential direction being defined by the relative positions of the object and of the second sensor, further comprising:
    a second sensor configured to create a third picture wherein the object is illuminated by the second X-ray source;
    a second mover for moving the second X-ray source or the object so as to change a second distance in the second preferential direction between the second X-ray source and the object, wherein
    the combiner is configured to combine the first, second and third pictures so as to acquire the multi-dimensional representation of the object.

7. The apparatus as claimed in claim 1, further comprising:
    a rotator for rotating the preferential direction by a predetermined angle with regard to the object.

8. The apparatus as claimed in claim 1, further comprising:
    a translator for performing a relative motion of the object and the first X-ray source in a lateral direction of motion that forms a predetermined angle with the preferential direction.

9. The apparatus as claimed in claim 8, wherein the translator is configured to move the first X-ray source in a direction perpendicular to the preferential direction.

10. The apparatus as claimed in claim 9, wherein the translator is configured to move the object in a direction perpendicular to the preferential direction.

11. A system for creating a multi-dimensional representation of an object, comprising:
- a first apparatus for creating a multi-dimensional representation of an object, comprising:
- an X-ray source for illuminating the object;
- a sensor located, in relation to the X-ray source, behind the object in a preferential direction defined by the relative positions of the object and of the sensor, for creating a first picture and a second picture of the object;
- a mover for moving the source or the object so as to change a distance in the preferential direction between the X-ray source and the object between the first and second pictures;
- a combiner configured to determine, from the change in the distance between the first and second pictures, an angle of rotation which describes a rotation of the X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object;
- a second apparatus for creating a multi-dimensional representation of an object, comprising:
- an X-ray source for illuminating the object;
- a sensor located, in relation to the X-ray source, behind the object in a preferential direction defined by the relative positions of the object and of the sensor, for creating a first picture and a second picture of the object;
- a mover for moving the source or the object so as to change a distance in the preferential direction between the X-ray source and the object between the first and second pictures;
- a combiner configured to determine, from the change in the distance between the first and second pictures, an angle of rotation which describes a rotation of the X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object; wherein
- the preferential direction of the first apparatus is perpendicular to the preferential direction of the second apparatus; and
- a common direction of motion so as to move the object in a direction of motion, which is perpendicular to the first and second preferential directions, in relation to the first and second apparatus.

12. A method of creating a multi-dimensional representation of an object, comprising:
- creating first and second pictures of the object illuminated using a first X-ray source using a sensor that is located, in relation to the first X-ray source, behind the object in a preferential direction defined by the relative positions of the object and of the sensor, a distance in the preferential direction between the first X-ray source and the object being different in the first picture than in the second picture;
- using a second X-ray source for illuminating the object;
- determining, from the change in the distance between the first and second pictures, an angle of rotation which describes a rotation of the first X-ray source in relation to the object, which rotation corresponds to a change in the perspective from which the object is illuminated and imaged on the sensor;
- combining the first and second pictures while using the angle of rotation and a computer tomography image processing algorithm in order to acquire the multi-dimensional representation of the object;
- wherein the second X-ray source is located in the preferential direction in front of the object, wherein the second X-ray source is moved in the preferential direction so as to change a second distance in the preferential direction between the second X-ray source and the object; and
- creating a third picture by the sensor, wherein the object is illuminated by the second X-ray source, wherein the combining further comprises combining the first, second and third pictures so as to acquire the multi-dimensional representation of the object.

13. A non-transitory storage medium having stored thereon a computer program comprising a program code for performing the method of creating a multi-dimensional representation of an object, said method comprising:
- creating first and second pictures of the object illuminated using a first X-ray source using a sensor that is located, in relation to the first X-ray source, behind the object in a preferential direction defined by the relative positions of the object and of the sensor, a distance in the preferential direction between the first X-ray source and the object being different in the first picture than in the second picture; and
- using a second X-ray source for illuminating the object;
- determining, from the change in the distance between the first and second pictures, an angle of rotation which describes a rotation of the first X-ray source in relation to the object, which rotation corresponds to a change in the perspective from which the object is illuminated and imaged on the sensor;
- combining the first and second pictures while using the angle of rotation and a computer tomography image processing algorithm in order to acquire the multi-dimensional representation of the object;
- wherein the second X-ray source is located in the preferential direction in front of the object, wherein the second X-ray source is moved in the preferential direction so as to change a second distance in the preferential direction between the second X-ray source and the object; and
- creating a third picture by the sensor, wherein the object is illuminated by the second X-ray source, wherein the combining further comprises combining the first, second and third pictures so as to acquire the multi-dimensional representation of the object.

14. An apparatus for creating a multi-dimensional representation of an object, comprising:
- an X-ray source for illuminating the object,
- a second X-ray source for illuminating the object;
- a sensor located, in relation to the X-ray source, behind the object in a preferential direction defined by the relative positions of the object and of the sensor, for creating a first picture and a second picture of the object;

a mover for moving the source or the object so as to change a distance in the preferential direction between the X-ray source and the object between the first and second pictures;

a combiner configured to determine, from the change in the distance between the first and second pictures, an angle of rotation which describes a rotation of the X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object, wherein the second X-ray source is located in the preferential direction in front of the object, wherein the mover is additionally configured to move the second X-ray source in the preferential direction so as to change a second distance in the preferential direction between the second X-ray source and the object, wherein the second X-ray source is arranged in front of the object with regard to a second preferential direction perpendicular to the preferential direction, said second preferential direction being defined by the relative positions of the object and of the second sensor, further comprising:

a second sensor configured to create a third picture wherein the object is illuminated by the second X-ray source;

a second mover for moving the second X-ray source or the object so as to change a second distance in the second preferential direction between the second X-ray source and the object, wherein the combiner is configured to combine the first, second and third pictures so as to acquire the multi-dimensional representation of the object.

15. An apparatus for creating a multi-dimensional representation of an object, comprising:

an X-ray source for illuminating the object, a second X-ray source for illuminating the object;

a sensor located, in relation to the X-ray source, behind the object in a preferential direction defined by the relative positions of the object and of the sensor, for creating a first picture and a second picture of the object;

a mover for moving the source or the object so as to change a distance in the preferential direction between the X-ray source and the object between the first and second pictures;

a combiner configured to determine, from the change in the distance between the first and second pictures, an angle of rotation which describes a rotation of the X-ray source in relation to the object and which corresponds to a change in the perspective from which the object is illuminated and imaged on the sensor; the combiner being further configured to combine the first and second pictures while using the angle of rotation and a computer tomography image processing algorithm in order to acquire the multi-dimensional representation of the object, wherein the second X-ray source is located in the preferential direction in front of the object, wherein the mover is additionally configured to move the second X-ray source in the preferential direction so as to change a second distance in the preferential direction between the second X-ray source and the object; and a translator for performing a relative motion of the object and the source in a lateral direction of motion that forms a predetermined angle with the preferential direction, wherein the translator is configured to move the source in a direction perpendicular to the preferential direction.

16. The apparatus as claimed in claim 15, wherein the translator is configured to move the object in a direction perpendicular to the preferential direction.

17. A method of creating a multi-dimensional representation of an object, comprising:

creating first and second pictures of the object illuminated using an X-ray source using a sensor that is located, in relation to the X-ray source, behind the object in a preferential direction defined by the relative positions of the object and of the sensor, a distance in the preferential direction between the X-ray source and the object being different in the first picture than in the second picture;

using a second X-ray source for illuminating the object;

determining, from the change in the distance between the first and second pictures, an angle of rotation which describes a rotation of the X-ray source in relation to the object, which rotation corresponds to a change in the perspective from which the object is illuminated and imaged on the sensor; and combining the first and second pictures while using the angle of rotation and a computer tomography image processing algorithm in order to acquire the multi-dimensional representation of the object, wherein the second X-ray source is located in the preferential direction in front of the object, wherein the second X-ray source is moved in the preferential direction so as to change a second distance in the preferential direction between the second X-ray source and the object, wherein the second X-ray source is arranged in front of the object with regard to a second preferential direction perpendicular to the preferential direction, said second preferential direction being defined by the relative positions of the object and of the second sensor, further comprising:

using a second sensor configured to create a third picture wherein the object is illuminated by the second X-ray source;

using a second mover for moving the second X-ray source or the object so as to change a second distance in the second preferential direction between the second X-ray source and the object, wherein combining comprises combining the first, second and third pictures so as to acquire the multi-dimensional representation of the object.

18. A method of creating a multi-dimensional representation of an object, comprising:

creating first and second pictures of the object illuminated using an X-ray source using a sensor that is located, in relation to the X-ray source, behind the object in a preferential direction defined by the relative positions of the object and of the sensor, a distance in the preferential direction between the X-ray source and the object being different in the first picture than in the second picture;

using a second X-ray source for illuminating the object;

determining, from the change in the distance between the first and second pictures, an angle of rotation which describes a rotation of the X-ray source in relation to the object, which rotation corresponds to a change in the perspective from which the object is illuminated and imaged on the sensor; and combining the first and second pictures while using the angle of rotation and a computer tomography image processing algorithm in order to acquire the multi-dimensional representation of the object, wherein the second X-ray source is located in the preferential direction in front of the object, wherein the second X-ray source is moved in the preferential direction so as to change a second distance in the preferential direction between the second X-ray source and the object, and performing, by a translator, a relative motion of the object and the source in a lateral direction of motion that forms a predetermined angle with the preferential direction, wherein the translator is configured to move the source in a direction perpendicular to the preferential direction.

19. A non-transitory storage medium having stored thereon a computer program comprising a program code for performing the method of claim 17.

20. A non-transitory storage medium having stored thereon a computer program comprising a program code for performing the method of claim 18.

* * * * *